US008806965B2

(12) United States Patent
Sato et al.

(10) Patent No.: US 8,806,965 B2
(45) Date of Patent: Aug. 19, 2014

(54) HEADSPACE SAMPLE INTRODUCTION DEVICE

(75) Inventors: Yosuke Sato, Kyoto (JP); Manabu Shimomura, Kyoto (JP); Akira Aono, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 725 days.

(21) Appl. No.: 13/133,626

(22) PCT Filed: Dec. 10, 2008

(86) PCT No.: PCT/JP2008/003690
§ 371 (c)(1),
(2), (4) Date: Jun. 8, 2011

(87) PCT Pub. No.: WO2010/067399
PCT Pub. Date: Jun. 17, 2010

(65) Prior Publication Data
US 2011/0239792 A1 Oct. 6, 2011

(51) Int. Cl.
*G01N 1/22* (2006.01)
*G01N 30/16* (2006.01)
G01N 1/40 (2006.01)
G01N 30/72 (2006.01)
G01N 35/10 (2006.01)

(52) U.S. Cl.
CPC .......... *G01N 1/2226* (2013.01); *G01N 1/4022* (2013.01); *G01N 30/7206* (2013.01); *G01N 2001/2229* (2013.01); *G01N 35/1095* (2013.01); *G01N 30/16* (2013.01)
USPC ..................................... 73/863.11

(58) Field of Classification Search
CPC .......... G01N 201/2226; G01N 1/2229; G01N 1/4022

USPC .................... 73/19.01, 863, 863.11
See application file for complete search history.

(56) References Cited

U.S. PATENT DOCUMENTS 5,792,423 A * 8/1998 Markelov .................... 422/83

FOREIGN PATENT DOCUMENTS

| JP | 09-307221 | 11/1997 |
| JP | 2002-005913 | 1/2002 |
| JP | 2008-169436 | 7/2008 |

OTHER PUBLICATIONS

Japanese language international preliminary report on patentability dated Jul. 5, 2011 and its English language translation for corresponding PCT application PCT/JP2008/003690.

*Primary Examiner* — Hezron E Williams
*Assistant Examiner* — David Z Huang
(74) *Attorney, Agent, or Firm* — Bingham McCutchen LLP

(57) ABSTRACT

A headspace sample introduction device which collects a sample gas from a sample container and introduces the gas into a predetermined analyzer is provided. The device includes a sample tray 10 capable of holding at least one sample container 100 storing a liquid sample or a solid sample, a heating means 30 for heating at least one sample container 100 taken from the sample tray 10, a sample-gas collecting means 40 for collecting a sample gas from the upper space in the sample container 100 held in the heating means 30, and a cooling transfer means 20 for keeping and cooling at least one sample container 100 taken from the heating means 30 and returning the cooled sample container 100 to the sample tray 20. Since the headspace sample introduction device can return the heated sample containers 100 to the sample tray 10 after they are cooled with the cooling transfer means 20, the hot sample containers can be assuredly prevented from contacting the user.

4 Claims, 2 Drawing Sheets

HEADSPACE SAMPLE INTRODUCTION DEVICE

CROSS-REFERENCE TO RELATED APPLICATIONS

This application is a national stage of international application No. PCT/JP2008/003690, filed on Dec. 10, 2008, which is incorporated herein by reference.

TECHNICAL FIELD

The present invention relates to a headspace sample introduction device which collects a sample gas volatilized from a liquid sample or a solid sample by a headspace method and introduces the sample gas into an analyzer such as a gas chromatograph or a gas chromatograph mass spectrometer.

BACKGROUND ART

A headspace analysis method is performed by heating a liquid sample or a solid sample stored in a container at a predetermined temperature for a predetermined period of time to volatilize components having relatively low boiling points, collecting a predetermined amount of gas containing these components from the upper space (headspace) of the container, and introducing the gas into an analyzer such as a gas chromatograph to analyze the gas. A chromatographic analysis employing this method is suitable, for example, for the measurement of flavor ingredients in food, the measurement of volatile organic compounds in water, or other measurements.

In headspace sample introduction devices used in headspace analyses of this kind, a plurality of sample containers (vials, etc.) are placed on a sample tray, and the sample containers are each sequentially transferred to an oven to be heated up to a predetermined temperature. Next, a sample gas is collected from the sample container with a needle and it is introduced into the analyzer. After collection of the sample gas, the sample container is returned to the sample tray. In conventional headspace sample introduction devices, the sample tray is disposed right above or below the oven. The sample containers are directly moved between the oven and the sample tray by a preset elevating means (for example, refer to Patent Document 1).

Patent Document 1: JP-A 2002-5913

DISCLOSURE OF THE INVENTION

Problem to be Solved by the Invention

Generally, headspace sample introduction devices can heat sample containers up to approximately 200° C. for volatilizing a sample. However, in conventional headspace sample introduction devices, the sample containers heated in the oven are returned without any treatment to the sample tray by the elevating means or other members. In a normal headspace analysis, a plurality of sample containers are set on a sample tray, and after completing collection of the sample gas and analysis with a gas chromatograph for all the sample containers, the used sample containers are removed from the sample tray. Although a user is thus not likely to contact the containers while they are hot, it is desirable to secure a more reliable measure for preventing the hot sample containers from contacting the user.

The present invention has been developed to solve the aforementioned problems, and the objective thereof is to provide a headspace sample introduction device capable of assuredly preventing hot sample containers from contacting the user.

Means for Solving the Problem

The present invention created to solve the aforementioned problems is a headspace sample introduction device for collecting a sample gas from a sample container and introducing the sample gas into a predetermined analyzer, including:

a) a sample tray capable of holding at least one sample container storing a liquid sample or a solid sample;

b) a heating means for heating at least one sample container taken from the sample tray;

c) a sample-gas collection means for collecting a sample gas from an upper space in the sample container heated with the heating means; and d) a cooling transfer means for holding and cooling at least one sample container after collection of the sample gas and returning the cooled sample container to the sample tray.

In the present invention, the term "cooling" refers to lowering the temperature. The cooling transfer means in the present invention may cool the sample container by natural air-cooling. However, the cooling transfer means may desirably have a structure which forcibly cools the sample container by generating airflows around the sample container with a blower, such as a fan, or by absorbing the heat from the sample container with a heat absorber utilizing a Peltier element or a refrigerant. This structure can shorten the time required for cooling the sample container.

In a desirable mode of the present invention, the cooling transfer means is constructed so as to transfer the sample container from the sample tray to the heating means and also transfer the sample container from the heating means to the sample tray, and the cooling transfer means is capable of holding a plurality of sample containers and performing the cooling of one sample container taken from the heating means in parallel with transfer of another sample container taken from the sample tray to the heating means.

The aforementioned structure does not need to have a separate mechanism for transferring the sample container from the sample tray to the heating means before collection of the sample gas. Therefore, a low cost of production with a reduced number of components can be achieved. Moreover, while cooling the sample container after collection of the sample gas, another sample container can be simultaneously transferred from the sample tray to the heating means. As a result, the sample containers can be cooled without lowering the efficiency for the introduction of the sample gas into an analyzer.

Preferably, the cooling transfer means is housed in a casing so as to assuredly prevent the hot sample containers held in the cooling transfer means from contacting the user.

Effect of the Invention

As described earlier, in the headspace sample introduction device according to the present invention, the heated sample container is cooled by the cooling transfer means and then returned to the sample tray. Therefore, the hot sample container can be assuredly prevented from contacting the user.

EXPLANATION OF NUMERALS

10 .... Sample Tray
12, 21, 34 .... Revolving Table
13, 24, 36 .... Motor
14, 22, 35 .... Vial Holder
15, 37 .... Shutter
20 .... Transfer Unit
30 .... Oven
31 .... Heat Insulating Block
32 .... Oven Tray
40 .... Gas Collector
41 .... Needle
50, 60, 70 .... Vial Elevating Mechanism
51, 61, 71 .... Rod
52, 62, 72 .... Rod Driver
80 .... Cooling Fan
90 .... Casing
100 .... Vial

BEST MODE FOR CARRYING OUT THE INVENTION

Figure 1:
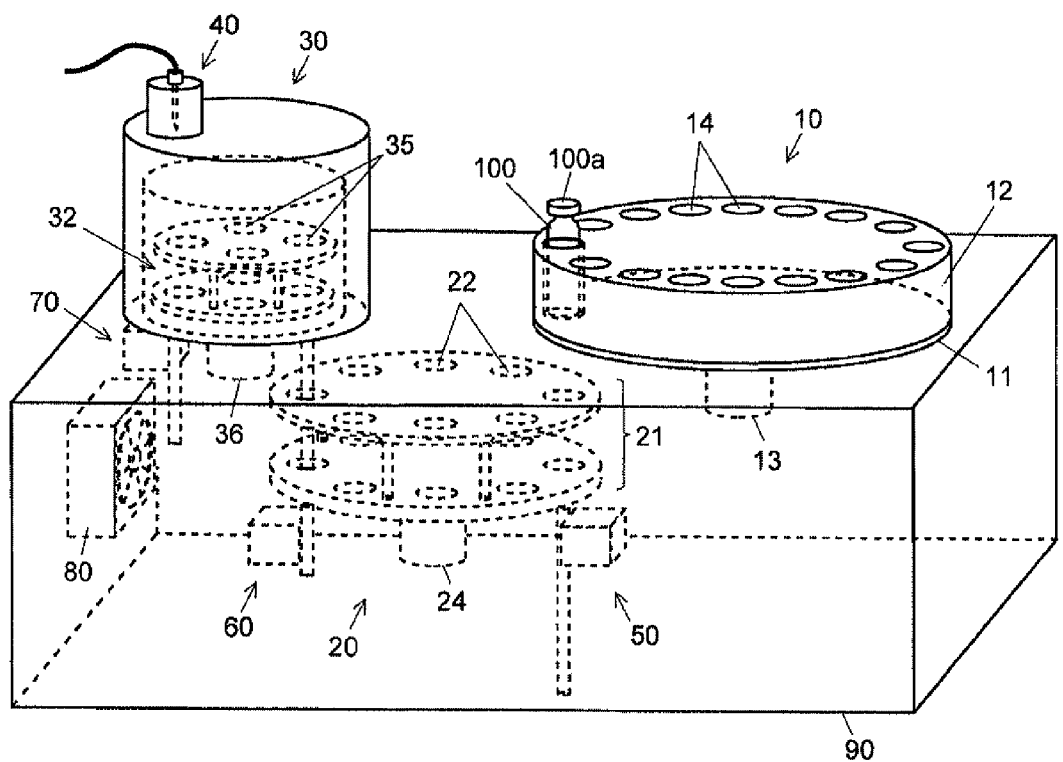
FIG. 1 is a perspective diagram showing a schematic configuration of a headspace sample introduction device according to the first embodiment of the present invention.
Figure 2:
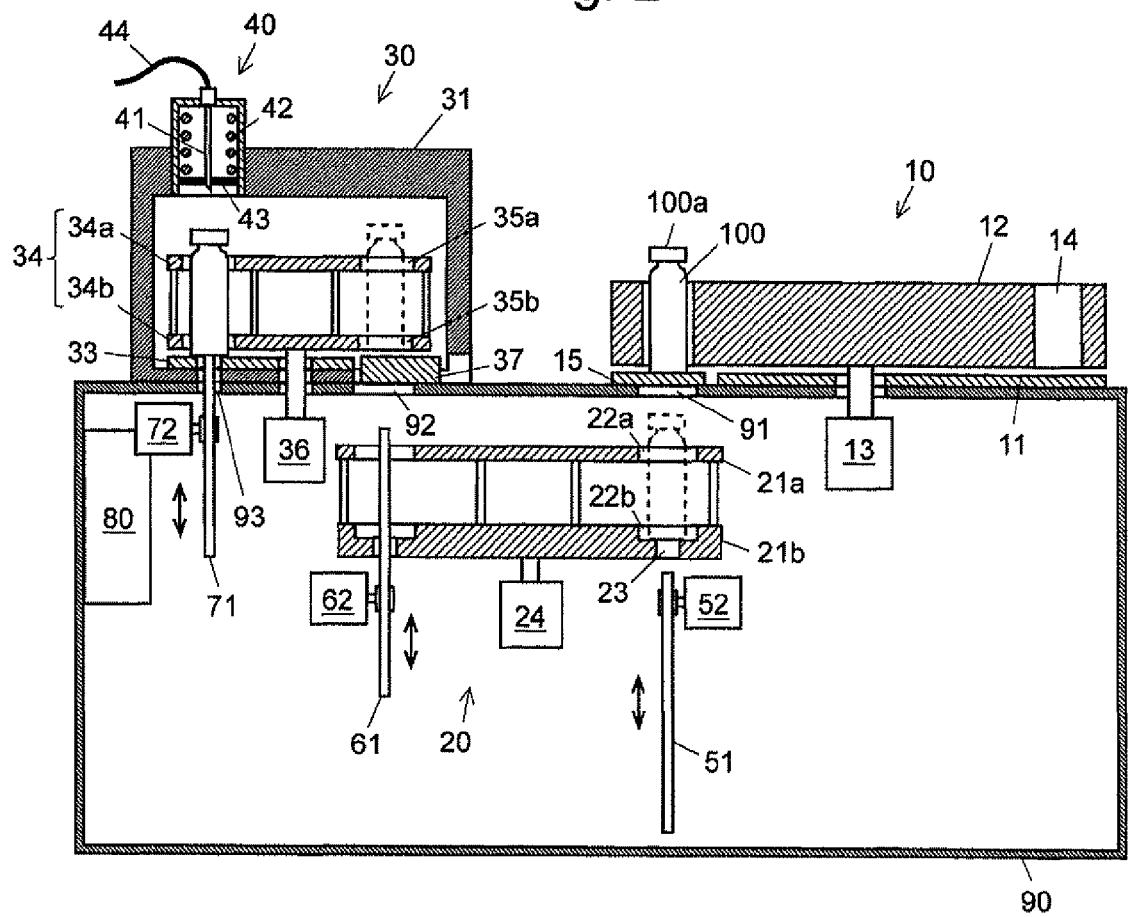
FIG. 2 is a cross-sectional diagram showing the headspace sample introduction device according to the embodiment.
Figure 3:
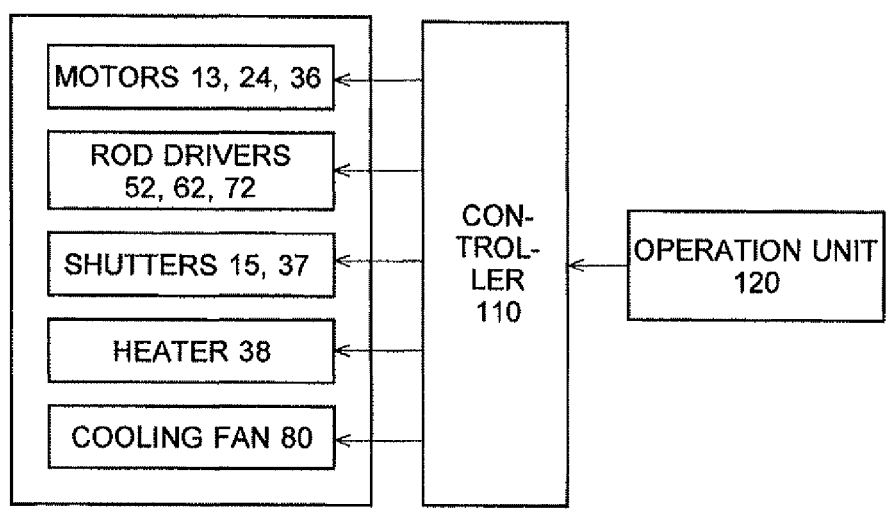
FIG. 3 is a block diagram schematically showing a control system of the headspace sample introduction device according to the embodiment.

One embodiment of a headspace sample introduction device of the present invention is hereinafter described with reference to the attached figures. FIG. 1 is a perspective diagram showing a schematic configuration of the headspace sample introduction device according to the present embodiment. FIG. 2 is a cross-sectional diagram of FIG. 1. FIG. 3 is a block diagram showing the configuration of the control system of the headspace sample introduction device according to the present embodiment.

The headspace sample introduction device of the present embodiment mainly includes a sample tray 10 on which vials (sample containers) 100 can be placed, a transfer unit 20, and an oven 30 for heating the vials 100. They are disposed on the upper side or inside a casing 90. A cooling fan 80 is mounted in the casing 90.

The sample tray 10 includes a circular base board 11 fixed on the upper surface of the casing 90, and a disk-shaped revolving table 12 which is mounted on the base board 11 and which can be rotationally driven by a motor 13. The revolving table 12 has a number of circularly-arranged vial holders 14 each formed of a through hole with a size big enough to just accept the vial 100. An opening 91 leading to the inside of the casing 90 is provided immediately below a position (hereinafter, referred to as position A) on the rotation track of the vial holders 14. The opening 91 can be closed by a shutter 15 which constitutes a part of the base board 11.

The oven 30 includes a heat insulating block 31 made of a heat-insulating material with a heater 38 (which is not shown in FIGS. 1 and 2) contained therein, and an oven tray 32 capable of holding a plurality of the vials 100. A gas collector 40 for collecting a sample gas from the vial 100 is mounted on the upper side of the oven 30. Similar to the aforementioned sample tray 10, the oven tray 32 includes a circular base board 33, and a disk-shaped revolving table 34 which is mounted on the base board 33 and which can be rotationally driven by a motor 36. The revolving table 34 includes two plates, an upper circular plate 34a and a lower circular plate 34b, which face each other and are fixed to one another with a predetermined distance between them so that the revolving table 34 has a round pillar shape as a whole. The upper circular plate 34a and the lower circular plate 34b are respectively provided with a plurality of circularly-arranged through holes 35a and a plurality of circularly-arranged through holes 35b located correspondingly to the through holes 35a. Each pair of the upper and lower through holes 35a and 35b forms one vial holder 35. An opening 92 leading to the inside of the casing is provided immediately below a position (hereinafter, referred to as position D) on the rotation track of the vial holders 35. The opening 92 can be closed by a shutter 37 which constitutes a part of the base board 33.

A gas collector 40 including a needle 41, a compression spring 42, and a movable plate 43 is disposed above another position (hereinafter referred to as position E) of the circular track of the vial holders 35. The needle 41 is inserted through an aperture formed in the center of the movable plate 43 with a tip end thereof pointing downward. The other end of the needle 41 is connected to a pipe 44 which reaches an analyzer such as a gas chromatograph at the outside of the oven 30. Below the position E, a vial elevating mechanism 70 is provided, which includes a rod 71 extending in a substantially vertical direction and a rod driver 72 for moving the rod 71 up and down. The rod 71 is capable of contacting a bottom surface of the vial 100 located at the position E, through a rod insertion opening 93 which penetrates through an upper surface of the casing 90, a bottom surface of the heat insulting block 31, and the base board 33. Meanwhile, the vial elevating mechanism 70 may move the rod 71 up and down with a linear motion that is converted from the rotation of a motor of the rod driver 72 by utilizing a rack attached to the rod 71 and a pinion attached to the motor. Alternatively, the vial elevating mechanism 70 may move the rod 71 up and down by means of an air cylinder or similar device provided in the rod driver 72.

The transfer unit 20 transfers the vials 100 between the sample tray 10 and the oven 30. This unit includes a revolving table 21 capable of carrying a plurality of the vials 100, a motor 24 for rotationally driving the revolving table 21, and two vial elevating mechanisms 50 and 60 located under the revolving table 21. Those structural elements are all housed in the casing 90.

The revolving table 21 includes two sheets of circular plates 21a and 21b which face each other and are fixed to one another with a predetermined distance between them so as to form a round pillar shape as a whole. The upper circular plate 21a has a plurality of circularly-arranged through holes 22a each having a slightly larger diameter than that of the vials 100. The lower circular plate 21b has concave portions 22b, each having approximately the same diameter as that of the through holes 22a, at positions corresponding to the respective through holes 22a formed in the upper circular plate 21a. Each upper through hole 22a is paired with one of the concave portion 22b to form one vial holder 22. Furthermore, each of the concave portions 22b has in its center a rod insertion opening 23 for allowing each of the rods 51 and 61 of the vial elevating mechanisms 50 and 60, respectively, to pass therethrough. The revolving table 21 of the transfer unit 20 is set in such a manner that a position (hereinafter referred to as position B) on the rotation track of the vial holders 22 is located immediately below the position A of the sample tray 10, and another position (hereinafter referred to as position C) on the rotation track of the vial holders 22 is located immediately below the position D of the oven tray 32. The aforementioned vial elevating mechanisms 50 and 60, each having the same structure as that of the vial elevating mechanism 70 located under the oven 30, are provided under the positions B and C, respectively.

A controller 110 including a CPU integrally controls the operations of the motors 13, 24, and 36 which respectively rotates the revolving tables 12, 21, and 34, the rod drivers 52, 62, and 72 of the vial elevating mechanisms 50, 60, and 70, the shutters 15 and 37, the cooling fan 80, the heater 38, as well as other components. An operation unit 120 is used to set various conditions, such as the temperature, heating time, and cooling time of the vials, the analysis cycle, as well as the sample collection amount.

A sequence of operations performed by the previously described system in collecting a sample gas volatilized from a sample liquid and introducing the sample gas into a gas chromatograph is hereinafter described.

A user pours respective sample liquids into a plurality of the vials 100, seals the vials 100 with rubber septums 100a, and sets the sealed vials at predetermined locations of the sample tray 10. When the user enters appropriate conditions and a command to initiate the operations through the operation unit 120, or when a command for initiating the analysis is given based on a predetermined time schedule, the motor 13 under control of the controller 110 rotates the revolving table 12. Upon arrival of a desired vial at the position A, the rod 51 moves upward and the shutter 15 opens so that the upper end of the rod 51 contacts the bottom surface of the vial 100. Then, the rod 51 moves downward, with the vial 100 passing through the opening 91 to be received by in the vial holder 22 of the transfer unit 20.

Upon completion of the transfer of the vial 100 to the transfer unit 20, the revolving table 21 of the transfer unit 20 rotates to transfer the vial 100 to the position C. Then, the shutter 37 opens and the rod 61 moves upward so that the vial 100 is lifted to the position D of the oven tray 32 and then received by the vial holder 35. The vial 100 is kept for a predetermined period of time in the oven 30 where the temperature is maintained at a predetermined value by the heater 38. During this period, volatilization of components from the sample liquid is promoted.

After the vial 100 is kept for the predetermined period of time in the oven 30, the gas collector 40 collects the sample gas in the following manner. First, the revolving table 34 of the oven tray 32 rotates to transfer the vial 100 to the position E. Then, the rod 71 pushes the vial 100 into the gas collector 40 so that the needle 41 pierces through the septum 100a of the vial 100. Accordingly, the gas phase portion in the vial 100 is introduced into the gas chromatograph. Upon completion of the sample gas introduction, the rod 71 moves downward to return the vial 100 to the oven tray 32. During this operation, a downward biasing force of the compression spring 42 is applied to the movable plate 43. As the rod 71 moves downward, the movable plate 43 pushes the vial 100 down. Thus, the needle 41 can be assuredly pulled out of the septum 100a.

Next, the revolving table 34 rotates to again transfer the vial 100 from which the sample gas has been collected to the position D. The vial 100 is lowered into the casing 90 by the vial elevating mechanism 60 and is then transferred to the revolving table 21 of the transfer unit 20. The vial 100 that has undergone the sample-gas collecting operation and is thus transferred to the transfer unit 20 is kept in the transfer unit 20 until a predetermined period of time elapses. During this period, the cooling fan 80 blows air to the vial 100 to cool the vial 100 and the sample liquid contained therein which have been heated to high temperatures in the oven 30. After the lapse of the predetermined period of time, the cooled vial 100 is returned to the sample tray 10 by the vial elevating mechanism 50. Alternatively, the revolving table 21 may be provided with a sensor such as a temperature sensor, and the vial 100 may be returned to the sample tray 10 when the temperature of the vial 100 reaches a predetermined value or lower.

Since the transfer unit 20 has a plurality of the vial holders 22, while one vial is being cooled in the previously described manner, other vials can be simultaneously transferred. Namely, while the vials after collection of the sample gas are held for cooling in a portion of the vial holders 22 of the transfer unit 20, other vials before collection of the sample gas can be transferred from the sample tray 10 into the oven 30 using the remaining vial holders 22. Accordingly, the vials can be cooled without lowering the sample introduction efficiency.

As described thus far, in the headspace sample introduction device according to the present embodiment, the transfer unit 20 is provided between the oven 30 and the sample tray 10, and the vial 100 taken from the oven 30 can be temporally kept for cooling in the transfer unit 20. Therefore, the vial can be returned to the sample tray 10 after its temperature is sufficiently decreased. Moreover, since the transfer unit 20 is housed in the casing 90, the hot vials have no chance of contacting the user's hand or the like before they are cooled.

It should be noted that the previous embodiment is a mere example of the present invention, and any modification or adjustment other than those described thus far can be made within the spirit of the present invention. For example, unlike the previous embodiment in which a cooling fan is provided in the casing, it is possible to naturally cool the vials rather than forcibly cooling them using the cooling fan or other cooling devices. Moreover, the cooling transfer means of the present invention may have various kinds of structures in addition to the structure of the previous embodiment in which the revolving table is rotationally driven. For example, a sector-shaped tray or a polygonal tray with the vial holders formed therein may be rotated or translated so as to transfer the sample container between the sample tray and the heater.

The invention claimed is:

1. A headspace sample introduction device for collecting a sample gas from a sample container and introducing the sample gas into a predetermined analyzer, including:
   a) a sample tray capable of holding at least one sample container storing a liquid sample or a solid sample;
   b) a heating unit for heating at least one sample container taken from the sample tray;
   c) a sample-gas collection unit for collecting a sample gas from an upper space in the sample container heated with the heating unit; and
   d) a cooling transfer unit for holding and cooling at least one sample container after collection of the sample gas and returning the cooled sample container to the sample tray, wherein:
   the cooling transfer unit is constructed so as to transfer the sample container from the sample tray to the heating unit and also transfer the sample container from the heating unit to the sample tray; and
   the cooling transfer unit is capable of holding a plurality of sample containers and performing cooling of one sample container taken from the heating unit in parallel with transfer of another sample container taken from the sample tray to the heating unit.

2. The headspace sample introduction device according to claim 1, wherein
   the cooling transfer unit includes a blowing unit for producing an air flow around the sample container held in the cooling transfer unit, or a heat-absorbing unit for absorbing the heat of the sample container held in the cooling transfer unit.

3. The headspace sample introduction device according to claim 2, wherein
the cooling transfer unit is housed in a casing.

4. The headspace sample introduction device according to claim 1, wherein
the cooling transfer unit is housed in a casing.

* * * * *